United States Patent
Mentink et al.

(10) Patent No.: US 11,690,795 B2
(45) Date of Patent: Jul. 4, 2023

(54) THICKENING AND STABILISING SYSTEM OF NATURAL ORIGIN SUITABLE, IN PARTICULAR, FOR PREPARING COSMETIC PRODUCTS

(71) Applicant: ROQUETTE FRERES, Lestrem (FR)

(72) Inventors: Léon Mentink, Lille (FR); Anne-Marie Lheritier, Cergy (FR); Marc Lavarde, Cergy (FR); Sophie Piot, Paris (FR)

(73) Assignee: Roquette Freres, Lestrem (FR)

( * ) Notice: Subject to any disclaimer, the term of this patent is extended or adjusted under 35 U.S.C. 154(b) by 379 days.

(21) Appl. No.: 16/770,389

(22) PCT Filed: Dec. 12, 2018

(86) PCT No.: PCT/FR2018/053236
§ 371 (c)(1),
(2) Date: Jun. 5, 2020

(87) PCT Pub. No.: WO2019/115944
PCT Pub. Date: Jun. 20, 2019

(65) Prior Publication Data
US 2021/0161795 A1    Jun. 3, 2021

(30) Foreign Application Priority Data

Dec. 13, 2017 (FR) ..................... 1762056

(51) Int. Cl.
*A61K 8/73* (2006.01)
*A61Q 19/00* (2006.01)

(52) U.S. Cl.
CPC ............. *A61K 8/732* (2013.01); *A61K 8/73* (2013.01); *A61K 8/731* (2013.01); *A61Q 19/00* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 3,086,890 A | 4/1963 | Sarko et al. | |
| 3,607,394 A | 9/1971 | Germino et al. | |
| 6,689,339 B1 | 2/2004 | Tanaka et al. | |
| 7,118,764 B2 | 10/2006 | Freres | |
| 7,378,085 B2 | 5/2008 | Oreal | |
| 10,398,631 B2 | 9/2019 | Oreal | |
| 2013/0059059 A1 | 3/2013 | Tristram et al. | |

FOREIGN PATENT DOCUMENTS

| DE | 19816664 A1 | 10/1999 | |
|---|---|---|---|
| FR | 2989892 A1 * | 11/2013 | ............... A61K 8/60 |
| JP | 2012205570 A | 10/2012 | |
| WO | 2009103052 A1 | 8/2009 | |
| WO | 2013119549 A1 | 8/2013 | |
| WO | 2013160349 A2 | 10/2013 | |

OTHER PUBLICATIONS

The English translation of the International Search Report, dated Mar. 14, 2019, in the corresponding PCT Appl No. PCT/FR2018/053236.
Fresenius Kabi. "Clear Thickener" Apr. 2016 (Apr. 2016), abstract No. Database accession Retrieved from: GNPD [online] MINTEL, XP002780834.
Gonzalez-Bermudez Carlos A et al. "Effect of adding different thickening agents on the viscosity properties andin vitromineral availability of infant formula," Food Chemistry, vol. 159, Mar. 12, 2014 (Mar. 12, 2014), pp. 5-11, ISSN: 0308-8146, XP028638688.
The English translation of the Japanese Office Action, dated Jul. 26, 2022, in the related Japanese Appl. No. 2020-532673.

* cited by examiner

*Primary Examiner* — Brian Gulledge

(57) ABSTRACT

Thickening system consisting of:
   a) at least one pregelatinized starch,
   b) at least one gum of plant or microbial origin,
   c) and at least one cellulose derivative.

Process for manufacturing a stable thickened system, by means of the steps of:
   a) providing an aqueous solution,
   b) heating the water to a temperature of between 20° C. and 80° C., preferentially between 20° C. and 50° C.,
   c) introducing into the aqueous solution at least one pregelatinized starch, at least one nonionic polysaccharide and at least one anionic polysaccharide,
   d) stirring the medium until dispersion of the constituents in the water is obtained.

15 Claims, No Drawings

THICKENING AND STABILISING SYSTEM OF NATURAL ORIGIN SUITABLE, IN PARTICULAR, FOR PREPARING COSMETIC PRODUCTS

This application is a National Stage Application of PCT/FR2018/053236 filed Dec. 12, 2018, which claims priority from French Patent Application No. 1762056, filed on Dec. 13, 2017. The priority of said PCT and French Patent Application are claimed. Each of the prior mentioned applications is hereby incorporated by reference herein in its entirety.

Cosmetic products are formulated products made from the mixing, combining or forming of multiple ingredients. For environmental and sustainability reasons, it is nowadays increasingly sought to formulate them from natural rather than synthetic ingredients. Natural polymers, in the form of gums and resins, which have been used for a long time as water-soluble binders, film-forming agents and also thickeners, are for this reason enjoying renewed interest.

Water is generally a very predominant ingredient in products of this type. It needs to be thickened, i.e. to have its viscosity increased so as to make the cosmetic products easier for the end user to handle and to apply, but also so as to give them a pleasant texture from a sensory viewpoint on the skin, the nails or the hair.

The industry initially made massive use of polymers of natural origin for this thickening and texturing function. However, these polymers had a certain number of drawbacks, notably in terms of color, odor, purity, consistency of efficiency and viscosifying quality. These reasons led to them being replaced with synthetic or semisynthetic polymers. In this respect, carbomers, which are widely used in cosmetics, are known. The Carbopol® range developed by the company Lubrizol is an example thereof. Mention may be made in particular of the product Carbopol® Ultrez 21, which is a synthetic acrylate copolymer, created to thicken, stabilize and afford suspension properties to a wide variety of cosmetic formulations.

However, the cosmetics industry must nowadays face up to new challenges in terms of protecting the environment, preserving our fossil resources, the carbon footprint and the safety and protection of consumers. From this point of view, it is reconsidering its formulations and returning as much as possible toward the use of solutions of natural origin for the formulation of its products. Science and technology are progressing in this field for the purpose of proposing reliable, efficient technical solutions enabling the formulator to efficiently thicken the products he makes, with natural ingredients, which are highly environmentally and consumer-friendly.

In this regard, the Applicant has succeeded in developing a novel thickening and stabilizing system, starting with a ternary mixture of at least one pregelatinized starch, of at least one gum of plant or microbial origin, and of at least one cellulose derivative. Starting with this combination, the Applicant has succeeded in developing a thickening system that is particularly well-suited to cosmetic formulations.

The thickening system according to the invention notably makes it possible to efficiently thicken aqueous solutions and to stabilize them, and to do so in an entirely unexpected and synergistic manner between its various constituents. In this respect, the viscosity obtained in the presence of the mixture is much higher than that observed for each of the constituents taken separately, or for combinations of only two of these constituents.

Furthermore, the thickening system according to the invention makes it possible to obtain very great stability of the viscosity, without any appreciable change in texture and without syneresis, and this being obtained over periods of several months. Such a result is particularly advantageous, and makes it possible to achieve the high level of stability required for cosmetic products in which said thickening system is liable to be used.

With regard to the viscosity and more particularly to the rheological behavior of the aqueous medium in which it is used, the thickening system according to the invention does not lead to any syneresis phenomenon, i.e. demixing of water with creation of a gel bathing in an aqueous phase, as is ordinarily observed for natural thickeners taken separately. This result is not only very interesting from an application viewpoint, but is also entirely surprising, since it is obtained only with the ternary combination used: the products, alone or used as a pair, lead to the prohibitive phenomenon of syneresis. From the sensory viewpoint, the thickening system according to the invention also leads to particularly interesting properties: very white, opaque products with a creamy texture are thus obtained, which places them as ideal candidates for thickening and stabilizing emulsions such as care creams or makeup creams. Furthermore, the products very advantageously appear to be non-greasy, non-runny and particularly soft and fresh.

Thus, a first subject of the present invention consists of a thickening system consisting of:
 a) at least one pregelatinized starch,
 b) at least one gum of plant or microbial origin,
 c) and at least one cellulose derivative.

The ternary thickening combinations according to the present invention comprise at least one pregelatinized starch as main component. Such starches in particular comprise pregelatinized alpha-glucose polymers of plant origin. Pregelatinized starches derived from corn, potato, wheat, rice, pea, oat, lentils, faba beans, broad beans, haricot beans and chickpeas, or combinations thereof are particularly preferred. Preferably, this pregelatinized starch is a waxy starch, i.e. rich in amylopectin and poor in amylose. It may notably be a waxy corn, potato or rice starch.

Pregelatinized starches are generally prepared via thermal, chemical or mechanical techniques that are liable to bring about simple swelling, partial splitting or even total dissolution of the starch granules so that they become water-soluble according to a "cold" process, i.e. by dispersion in water at a water temperature below 45° C., better still below 35° C. and even better still in the region of room temperature.

Thus, preferably, the pregelatinized starch no longer contains or virtually no longer contains any granules presenting a Maltese cross in polarized light.

The preferred techniques for obtaining a pregelatinized starch are techniques of cooking/drying of starch suspensions in aqueous medium notably such as atomization, drum cooking or extrusion. Autoclaving or indirect heating on a heat exchanger are cooking processes which are also possible and which tend to produce complex colloidal dispersions consisting of intact, fragmented and swollen granules. Examples of processes for preparing such starches will be found in U.S. Pat. Nos. 3,086,890, 3,607,394 or FR 2 822 471.

This pregelatinized starch may or may not be modified before or after the application of the cooking/drying treatment described above. In terms of modification, it may be a matter of one or more physical, physicochemical, chemical or enzymatic modifications. It may notably be a dextrinization, acid or enzymatic hydrolysis, carboxymethylation, hydoxypropylation, hydroxyethalion, acetylation, octenylsuccinylation, cationization, crosslinking or grafting treatment. Preferably, the pregelatinized starch is chosen from modified starches, notably dextrinized, hydrolyzed, carboxymethylated, hydroxypropylated, acetylated, octenylsuccinate or cationic, pregelatinized starches. More preferentially, the pregelatinized starch is chosen from carboxymethylated, hydroxypropylated, acetylated, octenylsuccinate pregelatinized starches.

It should be noted, however, that the thermal or mechanical techniques liable to give rise to simple swelling, partial splitting or even total dissolution of the starch granules so that they become water-soluble according to the "cold" process are not necessary when certain physicochemical or chemical modification treatments applied to the starch are sufficiently rigorous. Specifically, it is possible to use, as pregelatinized starch for the purposes of the invention, products which have only been dextrinized, hydrolyzed, cationized, hydroxypropylated or carboxymethylated no longer containing or virtually no longer containing any starch granules presenting a Maltese cross in polarized light.

In particular, nonionic pregelatinized starches are preferred, and notably those of the range sold by the Applicant under the brand name Pregeflo®. An example of such starches that are the most preferred is, for example, Pregeflo® CH 40.

Gums of plant or microbial origin that may be mentioned in particular include:
  gums derived from plant seeds or exudates, for instance gum arabic, konjac gum, guar gum, locust bean gum, gum tragacanth, tara gum, cassia gum, karaya gum, psyllium gum, pectin or derivatives and mixtures thereof;
  gums extracted from algae, for instance agar-agar, galactomannans, alginates or carrageenans, or derivatives and mixtures thereof;
  and gums derived from a microbial fermentation, for instance xanthans, gellans, mannans, scleroglucans or derivatives and mixtures thereof, and preferably a xanthan gum.

Preferably, this gum of plant or microbial origin used in the thickening system according to the invention is a nonionic polysaccharide. Gums derived from fermentation are preferred, for instance xanthans, gellans, mannans and scleroglucans, and in particular xanthans and scleroglucans, and more particularly xanthans. Such xanthan gums generally have a molecular weight of between 1000000 and 50000000 Da. Among the possible commercial products, examples that may be mentioned include the product Xanthan Gum FNCS-PC from the company: Jungbunzlauer International AG, the product Keltrol® CG-T from the company CP Kelco, the product Cosphaderm® X 17 from the company Cosphatec, the product Kahlgum 6673 FEE-Xanthan Gum from the company KahlWax, the products Rhodicare® S and Rhodicare® XC from the company Solvay and the product Vanzan® NF-C from the company Vanderbilt Minerals.

Cellulose derivatives that may be adopted include modified celluloses, notably methylcelluloses, hydroxyalkylcelluloses, ethylhydroxyethylcelluloses, methylethylcelluloses, carboxymethylcelluloses, hydroxypropylcelluloses and hydroxypropylmethylcelluloses; carboxymethylcelluloses and hydroxyethylcelluloses being preferred, hydroxyethylcelluloses being the most preferred. Mention may be made in particular of the following commercial products: Natrosol™ 250 HHR PC from Ashland Specialty Chemical; Espesante CH from Chemir; Tylose® H 15 YG4 from SE Tylose and Cellosize™ HEC QP 40 from DowDuPont (Dow).

Although the relative proportions between the various constituents of the ternary mixture are not fundamental, it is preferable, in order for the thickening system to be as efficient as possible, for the pregelatinized starch to be predominant relative to the thickening system as a whole, i.e. for it to represent more than 50% of the thickening system as a whole. Thus, the thickening system according to the invention will preferentially consist of:
  a) 1 to 12 parts by dry weight of at least one pregelatinized starch,
  b) 0.01 to 2 parts of at least one gum of plant or microbial origin,
  c) and 0.01 to 3 parts of at least one cellulose derivative.

More preferentially, it will consist of:
  a) 5 to 11 parts by dry weight of at least one pregelatinized starch,
  b) 0.1 to 1 part of at least one gum of plant or microbial origin,
  c) 0.1 to 2 parts and of at least one cellulose derivative.

Very preferentially, it will consist of:
  a) 6 to 10 parts by dry weight of at least one pregelatinized starch,
  b) 0.2 to 0.8 part of at least one gum of plant or microbial origin,
  c) 1 to 1.5 parts and of at least one cellulose derivative.

Another subject of the present invention consists of a process for manufacturing a stable thickened system, by means of the steps of:
  a) providing an aqueous solution,
  b) heating the water to a temperature of between 20° C. and 80° C., preferentially between 20° C. and 50° C.,
  c) introducing into the aqueous solution at least one pregelatinized starch, at least one nonionic polysaccharide and at least one anionic polysaccharide,
  d) stirring the medium until dispersion of the constituents in the water is obtained.

A person skilled in the art will know how to adapt the stirring speed of the medium, notably as a function of the amount of ingredients to be dispersed. However, a stirring speed of between 1000 and 5000 rpm appears to be entirely acceptable.

It is, moreover, clearly understood that the process according to the invention incorporates all the features listed above relating to the ternary system manufactured according to said process.

This thickened system proves to be very stable and non-allergenic to the skin. It furthermore offers the advantage of having of giving consistency of viscosity and of texture, independently of the pH or of the presence of electrolytes. In other words, this system is not affected by the pH of the medium, or by the presence of monovalent, divalent or trivalent salts. This criterion is all the more important since, in general, products for cosmetic use and notably for topical application are liable to be subjected or exposed to pH variations (by way of example, the pH of the skin is slightly acidic, and ranges between 4 and 6). Having a product which does not have any particular limit for use in terms of pH or of presence of salts thus represents a very great technical advantage for a cosmetic composition.

Finally, a final subject of the invention consists of a cosmetic composition containing the thickened and stable system according to the invention.

Specifically, the thickened and stable system in accordance with the invention allows the easy production of emulsions that are both very stable and very fine, which have modulable textures and a fresh, silky and non-greasy feel, even for high contents of dispersed fatty phase. It is thus possible to obtain emulsions that have a good emollient effect on the skin and also a good moisturizing effect on the upper layers of the epidermis.

Said cosmetic composition may notably be a care product, such as a moisturizing, antiwrinkle, antiaging, slimming, antichant or firming composition, a body balm or a beauty mask and may be in the form of thickened solutions, gels, milks, creams, suspensions, aerosols or mousses.

Said cosmetic composition may notably be a makeup product for the eyes, such as a mascara, a liner, or a makeup product for the face, such as a powder, a foundation, for the face, or a makeup product for the nails, such as varnish, or a makeup product for the lips, such as a lipstick or a lip gloss.

Said cosmetic composition may notably be a sun product, for instance a protective product or a self-tanning product.

Said cosmetic composition may notably be a body hygiene product, for instance a soap, a hair remover or a deodorant.

Said cosmetic product may notably be a haircare product, for instance a shampoo, a coloring, a dye or a permanent-waving product, a lotion for preventing hair loss, a lacquer or a fixative.

Said cosmetic composition may notably be fragrance, an eau de toilette or an eau de parfum.

The examples which follow make it possible to better understand the present invention, without however limiting the scope thereof.

EXAMPLES

Throughout the examples, various formulations were prepared, with the following products:
Pregeflo CH 40 sold by the company Roquette Freres
Xanthan gum sold by the company CP Kelco under the name Keltrol® CG-T
Hydroxyethylcellulose (HEC) sold by the company Ashland Specialty Chemical under the name Natrosol™ 250 HHR PC Unless otherwise specified, all the formulations were prepared in the following manner:
1) Weigh out and mix the various thickeners
2) Heat the water to 40° C.
3) Using a turbomixer stirring at 2000 rpm, disperse the mixture of ingredients added gradually
4) Leave stirring until the emulsion is at room temperature.

All the viscosities are determined using a Brookfield DV-II+ Pro viscometer.

Example 1

This example illustrates the synergistic effect between the three constituents of the system, for thickening an aqueous solution. Table 1 below shows the weight percentage in water of each constituent, used alone, as a binary mixture, or as a ternary system. The thickening system according to the invention advantageously leads to the highest viscosity, while at the same time giving the most pleasant texture on the skin.

TABLE 1

| Ingredients | Viscosity (mPa · s) |
| --- | --- |
| 2.5% Pregeflo CH 40 | 15 (SP3) |
| 0.7% Xanthan gum | 1 330 (SP3) |
| 0.7% Hydroxyethylcellulose | 770 (SP3) |
| 0.7% Xanthan gum + 0.7% hydroxyethylcellulose | 4470 (SP4) |
| 2.5% Pregeflo CH 40 + 0.7% xanthan gum + 0.7% hydroxyethylcellulose | 11 135 (SP4) |

Example 2

This example illustrates the syneresis effect observed, for control compositions not containing all three ingredients which constitute the thickening system according to the invention. Table 2 below shows the weight percentage in water of each constituent used, for the various combinations prepared. In all the cases, another constituent was added, which was the starch M-DF 12 S, a granular starch rather than a pregelatinized starch as defined above, but which has no real influence on the viscosity.

It is found that all the systems outside the invention lead to very pronounced syneresis, which is a prohibitive point for their use in cosmetic formulations.

TABLE 2

| PREGEFLO CH 40 | Xanthan gum | HEC | Starch MDF 12S | Viscosity (mPa · s) 48 hours at room temp. |
| --- | --- | --- | --- | --- |
| 1.5 | 0 | 0.7 | 1.8 | Syneresis |
| 2.5 | 0 | 0 | 1.5 | Syneresis |
| 1.9 | 0 | 0 | 2.1 | Syneresis |
| 1.5 | 0 | 0.7 | 1.8 | Syneresis |
| 1.9 | 0 | 0.5 | 1.6 | Syneresis |

Example 3

This example illustrates the change in viscosity observed for aqueous solutions thickened with various thickening systems according to the invention, after 15 days, depending on whether said aqueous solutions were stored at 4, 40 or 50° C. Table 3 demonstrates noteworthy maintenance of the viscosity at all of these temperatures: there is virtually no influence of the storage temperature.

TABLE 3

| | | | Viscosity (mPa · s) | | |
| --- | --- | --- | --- | --- | --- |
| % Pregeflo CH40 | % xanthan gum | % hydroxyethyl cellulose | After 15 days at 4° C. | After 15 days at 40° C. | After 15 days at 50° C. |
| 2.5 | 0.3 | 0.2 | 7 100 (SP4) | 6 650 (SP4) | 7 550 (SP4) |
| 4 | 0.6 | 0.2 | 12 650 (SP5) | 11 200 (SP5) | 13 000 (SP5) |
| 4 | 0.3 | 0.8 | 31 000 (SP6) | 28 000 (SP6) | 27 700 (SP6) |
| 3.25 | 0.45 | 1 | 35 500 (SP6) | 31 000 (SP6) | 34 150 (SP6) |
| 4 | 0.3 | 0.2 | 15 300 (SP6) | 13 400 (SP6) | 14 500 (SP6) |
| 4.5 | 0.45 | 0.5 | 27 000 (SP6) | 21 000 (SP6) | 23 050 (SP6) |
| 2.5 | 0.3 | 0.8 | 23 000 (SP6) | 20 000 (SP6) | 23 300 |

TABLE 3-continued

| % Pregeflo CH40 | % xanthan gum | % hydroxyethyl cellulose | Viscosity (mPa · s) | | |
|---|---|---|---|---|---|
| | | | After 15 days at 4° C. | After 15 days at 40° C. | After 15 days at 50° C. |
| 3.25 | 0.45 | 0.5 | 16 500 (SP6) | 16 500 (SP6) | 17 500 (SP6) |
| 2.5 | 0.6 | 0.8 | 25 000 (SP6) | 25 700 (SP6) | 24 000 (SP6) |
| 2 | 0.45 | 0.5 | 10 700 (SP6) | 9 100 (SP6) | 10 100 (SP6) |
| 4 | 0.6 | 0.8 | 33 000 (SP6) | 33 000 (SP6) | 34 000 (SP6) |
| 2.5 | 0.6 | 0.2 | 10 600 (SP6) | 9 700 (SP6) | 10 500 (SP6) |
| 3.25 | 0.45 | 0 | 7 000 (SP6) | 7 500 (SP6) | 9 300 (SP6) |
| 3.25 | 0.7 | 0.5 | 18 000 (SP6) | 17 500 (SP6) | 19 200 (SP6) |
| 3.25 | 0.2 | 0.5 | 15 400 (SP6) | 15 100 (SP6) | 17 000 (SP6) |

Example 4

This example illustrates the change in various sensory parameters observed for aqueous solutions thickened with various thickening systems according to the invention, after 48 hours. Table 4 demonstrates that all of the formulations tested make it possible to obtain a satisfactory sensory configuration. In particular, a product that is sparingly runny, with a descriptor of less than or equal to 3, which spreads well, with a spreading descriptor of greater than or equal to 5 and usually greater than or equal to 7, sparingly tacky, with a corresponding descriptor of less than or equal to 4, and penetrating, with a corresponding sensory descriptor of greater than or equal to 6, is always obtained. With the exception of certain formulations rich in hydroxyethylcellulose, very white formulations, with whiteness descriptors of greater than or equal to 6, are obtained on the whole.

The invention thus makes it possible to obtain products that are satisfactory from a sensory viewpoint.

| % PREGEFLO CH40 | % Xanthan gum | % HEC | Sensory evaluations after 48 hours | | | | |
|---|---|---|---|---|---|---|---|
| | | | White | Runny | Spreading | Tack | Penetrating |
| 2.5 | 0.3 | 0.2 | 7 | 2 | 8 | 2 | 8 |
| 4 | 0.6 | 0.2 | 7 | 3 | 7 | 0 | 8 |
| 4 | 0.3 | 0.8 | 6 | 3 | 5 | 3 | 6 |
| 3.25 | 0.45 | 1 | 3 | 2 | 5 | 3 | 6 |
| 4 | 0.3 | 0.2 | 9 | 2 | 7 | 2 | 7 |
| 4.5 | 0.45 | 0.5 | 6 | 3 | 5 | 4 | 8 |
| 2.5 | 0.3 | 0.8 | 8 | 2 | 7 | 0 | 6 |
| 3.25 | 0.45 | 0.5 | 8 | 3 | 7 | 0 | 9 |
| 2.5 | 0.6 | 0.8 | 5 | 2 | 5 | 1 | 7 |
| 2 | 0.45 | 0.5 | 8 | 1 | 7 | 2 | 7 |
| 4 | 0.6 | 0.8 | 4 | 3 | 7 | 2 | 8 |
| 2.5 | 0.6 | 0.2 | 9 | 3 | 9 | 3 | 7 |
| 3.25 | 0.45 | 0 | 9 | 3 | 8 | 3 | 7 |
| 3.25 | 0.7 | 0.5 | 8 | 2 | 8 | 3 | 8 |
| 3.25 | 0.2 | 0.5 | 9 | 2 | 8 | 4 | 8 |

The invention claimed is:

1. A thickening system, consisting of:
a) at least one pregelatinized starch,
b) at least one gum of plant or microbial origin, and
c) and at least one cellulose derivative.

2. The thickening system as claimed in claim 1, characterized in that the pregelatinized starch is obtained from corn, potato, wheat, rice, pea, oat, lentils, *faba* beans, broad beans, haricot beans and chickpeas, or combinations thereof.

3. The thickening system as claimed in claim 1, characterized in that the pregelatinized starch is obtained from a waxy starch.

4. The thickening system as claimed in claim 3, characterized in that the pregelatinized starch is obtained from a corn starch, potato starch or a rice starch.

5. The thickening system as claimed in claim 1, characterized in that the gum of plant or microbial origin is a gum obtained from plant seeds or exudates, a gum extracted from algae or a gum obtained from microbial fermentation or derivatives thereof.

6. The thickening system as claimed in claim 5, characterized in that the gum of plant or microbial origin is a xanthan gum.

7. The thickening system as claimed in claim 1, characterized in that the cellulose derivative is chosen from modified celluloses.

8. The thickening system as claimed in claim 7, characterized in that the cellulose derivative is methylcelluloses, hydroxyalkylcelluloses, ethylhydroxyethylcelluloses, methylethylcelluloses, carboxymethylcelluloses, hydroxypropylcelluloses or hydroxypropylmethylcelluloses.

9. The thickening system as claimed in claim 8, characterized in that the cellulose derivative is carboxymethylcelluloses or hydroxyethylcelluloses.

10. The thickening system as claimed in claim 9, characterized in that the cellulose derivative is hydroxyethylcelluloses.

11. The thickening system as claimed in claim 1, characterized in that it consists of:
a) 1 to 12 parts by dry weight of at least one pregelatinized starch,
b) 0.01 to 2 parts of at least one gum of plant or microbial origin, and
c) 0.01 to 3 parts of at least one cellulose derivative.

12. The thickening system as claimed in claim 11, characterized in that it consists of:
a) 5 to 11 parts by dry weight of at least one pregelatinized starch,
b) 0.1 to 1 part of at least one gum of plant or microbial origin, and
c) 0.1 to 2 parts of at least one cellulose derivative.

13. The thickening system as claimed in claim 12, characterized in that it consists of:
- a) 6 to 10 parts by dry weight of at least one pregelatinized starch,
- b) 0.2 to 0.8 part of at least one gum of plant or microbial origin, and
- c) 1 to 1.5 parts of at least one cellulose derivative.

14. A cosmetic composition, comprising the thickening system according to claim 1.

15. The cosmetic composition as claimed in claim 14, wherein said cosmetic composition is a makeup product for the eyes, a sun product, a body hygiene product, a haircare product or a fragrance.

\* \* \* \* \*